(12) United States Patent
Morikawa et al.

(10) Patent No.: US 6,800,482 B2
(45) Date of Patent: Oct. 5, 2004

(54) **CULTURED CELLS OF AUSTRALIAN LAUREL, *PITTOSPORACEAE* AND A METHOD FOR CULTURING TISSUES BY USING SAID CULTURED CELLS**

(75) Inventors: Hiromichi Morikawa, Higashihiroshima (JP); Misa Takahashi, Higashihiroshima (JP)

(73) Assignee: Hiroshima University, Higashihiroshima (JP)

( * ) Notice: Subject to any disclaimer, the term of this patent is extended or adjusted under 35 U.S.C. 154(b) by 0 days.

(21) Appl. No.: 09/908,632

(22) Filed: Jul. 20, 2001

(65) Prior Publication Data

US 2002/0137206 A1 Sep. 26, 2002

(30) Foreign Application Priority Data

Jan. 19, 2001 (JP) .......................................... 2001-11435

(51) Int. Cl.$^7$ ............................. C12N 5/00; C12N 5/02; C12N 5/04; C12N 5/10; C12N 5/14; C11N 5/02
(52) U.S. Cl. .................... 435/430; 435/420; 435/430.1; 435/419; 435/430; 435/410; 800/295; 800/298; 800/323
(58) Field of Search ............................... 435/420, 430, 435/430.1, 450

(56) References Cited

U.S. PATENT DOCUMENTS

| | | | | | |
|---|---|---|---|---|---|
| 5,304,725 | A | * | 4/1994 | Nelson | ........................ 800/200 |
| 5,589,613 | A | * | 12/1996 | Firoozabady et al. | ....... 800/205 |
| 5,792,927 | A | * | 8/1998 | Firoozabady et al. | ....... 800/205 |
| 5,840,581 | A | * | 11/1998 | Carraway et al. | ........ 435/430.1 |

OTHER PUBLICATIONS

Anonymous. *Pittosporum tobira*. http://ag.arizona.edu/pima/gardening/aridplants/Pittosporum_tobira.html.*

L. Waston and M. J. Dallwitz. The Families of Flowering Plants: Descriptions, Illustrations, Identification and Information Retrieval. Version: Dec. 14, 2000. Http://biodiveristy.uno.edu/delta/'.*

Zamora et al. "Tissue culture of *Pittosporum pentandrum* (BI.) Merr. (Mamalis) and plantlet regeneration of *P. resinifererum* Hemsi (hanga–hanga)" University of the Phillippines Research Digest, Dec. 1995.*

Williams et al. "Auxin type, gel concentration, rooting and survival of *Cheiranthera volubilis* in vitro". HortScience vol. 24 (2): pp. 305–307 1989.*

Bruschi et al. "In vitro growth and morphogenetic response of *Pittosporum tobira* Ait. and *Nicotiana tabacum* L. to surfactants." Advances in Horticultural Science vol. 11 (1) pp. 17–24 1997.*

Vargas–Zamora "Tissue Culture of Petroleum Nut Tree (*Pittosporum resiniferum* Hemsl.)" Biotechnol. Forest Tree Improvement (27–34) 1992.*

Zamora "Tissue Culture of *Pittosporum resiniferum* Hemsl. (Petroleum nut tree)" Science Diliman, v. 3 pp. 46–66 1990.*

Carl A. Huetteman et al., "Thidiazuron: a Potent Cytokinin for Woody Plant Tissue Culture", *Plant Cell, Tissue and Organ Culture*; vol. 33, pp. 105–119, 1993, Kluwer Academic Publishers, Netherlands.

R. Gill et al., "Thidiazuron–Induced Highley Morphogenic Callus and High Frequency Regeneration of Fertile Peanut (*Arachis Hypogeea L.*) Plants", *In Vitro Cell. Biol.–Plant*, vol. 35, pp. 445–450, Nov. Dec. 1999, Society for In vitro Biology.

* cited by examiner

Primary Examiner—Bruce R. Campell
Assistant Examiner—W. C. Haas
(74) Attorney, Agent, or Firm—Burns, Doane, Swecker & Mathis, L.L.P.

(57) ABSTRACT

The present inventors provide a method of culturing an undifferentiated *Pittosporum tobira* cell, which is obtained by culturing a *Pittosporum tobira* tissue in a culture medium containing thidiazuron (TDZ) in an amount effective for inducing callus formation. The present inventors further provide a method for regenerating a *Pittosporum tobira* plantlet. This method comprises the step of subculturing a cultured cell in a culture medium containing thidiazuron (TDZ) in an amount effective for inducing callus formation.

13 Claims, 1 Drawing Sheet

(1 of 1 Drawing Sheet(s) Filed in Color)

CULTURED CELLS OF AUSTRALIAN LAUREL, PITTOSPORACEAE AND A METHOD FOR CULTURING TISSUES BY USING SAID CULTURED CELLS

BACKGROUND OF THE INVENTION

The present invention relates to cultured cells and a tissue-culturing method, and particularly to cultured cells of the Australian laurel (including house-blooming mock orange, Japanese pittosporum and mock orange), Pittosporaceae and a method for culturing tissues of the Australian laurel, Pittosporaceae by using the cultured cells.

Tissue culture of higher plants have been recently investigated, and techniques for culturing plant tissues taken out from leaves, stems, roots, etc. in large quantities have been noted. If a plant piece cut is placed in a culture medium such as agar or liquid containing a nutrient, a mass of cells swell up from the cut portion. This is called "callus".

In general, cells of different tissues, for example, tissues of a root and a leaf differ from each other in shape and function. This results from a phenomenon that the cells gradually differentiate with growth. However, the callus continues to grow, while being adventive and undifferentiated.

Ordinarily, in order to propagate plants, seeds or cuttings must be planted. Growing thereof is largely influenced by soils and environments. However, the culture of the callus is not influenced by changes in soils or environments. Further, the callus more fast grows than the ordinary plants. When the callus is supplied with a hormone or a chemical material for promoting germination or rhizogenesis, it becomes a complete plant.

In order to culture tissues of such calluses, methods for culturing tissues of trees such as poplars or eucalyptus are known.

However, the trees for which the tissue culture has been established are limited to kinds of timers such as poplars and eucalyptus. This is one of partially because it is difficult to grow or radicate other kinds without appropriate hormones.

The Australian laurel, Pittosporaceae is a plant belonging to Pittosporaceae for buckbushes and boulevard trees, and a boulevard tree planted in a road center strip. The Australian laurel, Pittosporaceae is strong against environmental pollution and saline resistant. In order to assuredly and speedily supply such plants being strong against environmental pollution, the tissue culture is effective. However, a method for stably proliferating the Australian laurel, Pittosporaceae in a large quantity has not been established.

SUMMARY OF THE INVENTION

Under these circumstances, it is an object to provide cultured cells and tissue culture to establish stable mass proliferation and transformation system for the Australian laurel, Pittosporaceae.

In order to accomplish the above object, the present inventors repeatedly effected fundamental researches with respect to conditions suitable for inducing callus-formation and redifferentiation of the Australian laurel, Pittosporaceae. As a result, the inventors discovered the cultured cells and the tissue-culturing method according to the present invention.

The Australian laurel, Pittosporaceae cultured cell is an undifferentiated cell and is obtained by culturing a part of a tissue of the Australian laurel, Pittosporaceae in a culture medium containing thidiazuron (TDZ) in an amount effective for inducing a callus of the Australian laurel, Pittosporaceae tissue.

Following are preferred embodiments of the Australian laurel, Pittosporaceae cultured cells according to the present invention. Any combination thereof are considered to be preferred embodiments of the invention, so long as such will afford no adverse effect.
(1) The Australian laurel, Pittosporaceae tissue is selected from the group consisting of a stem, a leaf, a germ cell and a root.
(2) The cultured cell is a tissue having an age of less than 8 weeks after sowing a Australian laurel, Pittosporaceae seed.
(3) The Australian laurel, Pittosporaceae tissue is a tissue obtained by aseptically growing the Australian laurel, Pittosporaceae seed.
(4) The Australian laurel, Pittosporaceae tissue is a tissue in which a foreign material is introduced into an explant of the seedling of the Australian laurel, Pittosporaceae.
(5) The foreign material is at least one selected from the group consisting of a hereditable material, a protein, an organelle, a physiologically active material and an indicator.
(6) The hereditable material is at least one selected from the group consisting of a DNA, a RNA, an origonucleotide, a plasmid, a chromosome, a artificial chromosome, an organelle DNA and a nucleic acid analog.
(7) The medium further contains naphthaleneacetic acid (NAA).

The present invention further relates to a method for regenerating a plantlet of a Australian laurel, Pittosporaceae, said method comprising the step of subculturing the cultured cell as mentioned above in a culture medium containing thidiazuron (TDZ) in an amount effective for inducing a callus of the Australian laurel, Pittosporaceae tissue.

The following are preferred embodiments of the Australian laurel, Pittosporaceae plantlet-regenerating method.
(1) The culture medium further contains naphthaleneacetic acid (NAA).
(2) The culture is a WP culture.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

For a better understanding of the invention, reference is made to the attached drawing, wherein.

BRIEF DESCRIPTION OF THE INVENTION

Figure 1:
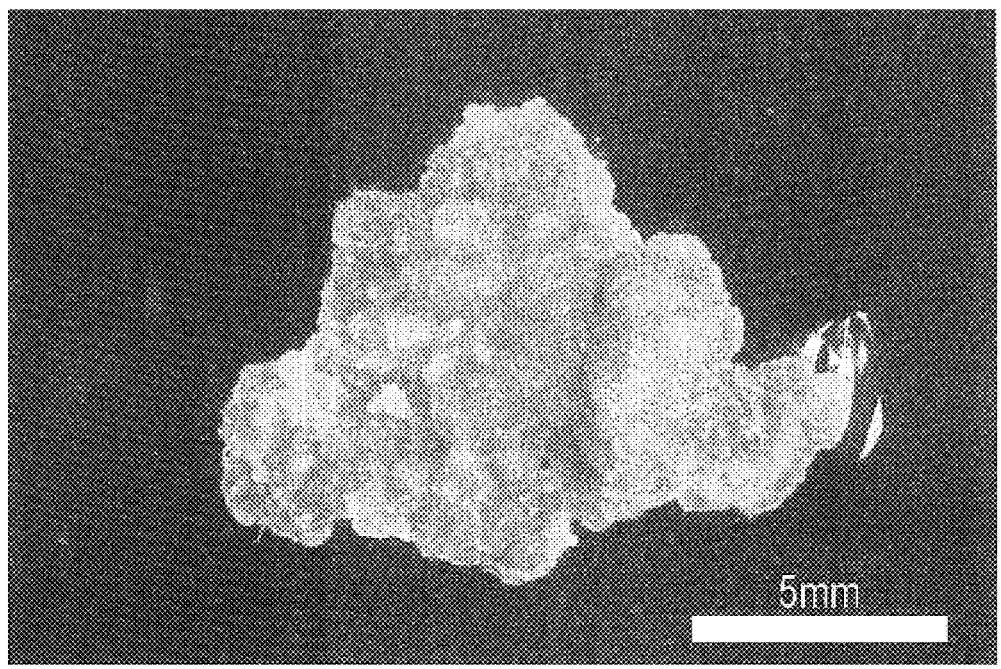
FIG. 1 is a microscope photograph showing the appearance of a Australian laurel, Pittosporaceae into which a gene is introduced.

The present invention will be explained in more detail with reference to the drawing.

The cultured cell according to the present invention is a cultured cell of the Australian laurel, Pittosporaceae which has a undifferential power and is obtained by culturing a part of a tissue of the Australian laurel, Pittosporaceae in a culture containing thidiazuron (TDZ) in an amount effective for inducing a callus of the Australian laurel, Pittosporaceae. A plantlet is generally formed according to a tissue-culturing method through the steps of 1̂ production of the callus, 2̂ formation of multiple shoots from the callus, 3̂ redifferentiation of the polyblast and 4̂ formation of the plantlet. The tissue culture of the Australian laurel, Pittosporaceae also passes this steps of the formations. Here, the polyblast is a number of shoots gathered, and the cell means a differentiated state. In the following, the cultured cells and the tissue culturing method for the Australian laurel, Pittosporaceae will be explained.

Although not limited, tissues such as stems, leaves, roots, shoot tips, root ends and germ cells may be recited as the Australian laurel, Pittosporaceae tissues.

Although Australian laurel, Pittosporaceae tissues may be ones taken out from matured Australian laurel, Pittosporaceae trees, those tissues are preferably relatively young cell tissues obtained after planting Australian laurel, Pittosporaceae seeds. For example, the tissues obtained less than 8 weeks after planting the Australian laurel, Pittosporaceae seed is preferred.

The Australian laurel, Pittosporaceae seed may be planted through aseptically germinating and growing it in a culture medium. The aseptic treatment is not limited to any one, and can be effected, for example, by treating the culture medium with ethanol or the like for a few to several hours and with sodium hypochlorite for a few to several hours, and washing the resultant with sterilized water. The seed is preferably used after being kept in a dark place at 4 to 10° C. for one to three days while being supplied with water. The seed is planted in this culture medium.

The cultured cells according to the present invention can be obtained by culturing a part of the above tissue in a culture containing thidiazuron (TDZ). The amount of thidiazuron, which depends upon the culture and the culturing condition employed, is preferably 10 to $10^2$ $\mu$M. This range is preferable, because if the amount is less than 10 $\mu$M or more than $10^2$ $\mu$m, it is difficult to maintain the redifferentiated rate. No limitation is posed upon the culture containing thidiazuron. For example, WP culture medium, MS culture medium, white culture medium and modified culture media thereof may be recited. The WP culture medium is a culture medium modified from the MS culture medium for the purpose of stem tip-culturing of and mass culturing rosebay *Kalmia latiflora* in the Elicaceae group. The MS culture medium is a culture developed for the proliferation of pith tissue of tobacco and the callus. The WP culture medium is preferably used in culturing the Australian laurel, Pittosporaceae from the standpoint of enhancing the callus-forming rate and the redifferentiation rate.

In the present invention, the culture medium may further contain naphthaleneacetic acid (NAA). The amount of naphthaleneacetic acid, which depends upon other culturing condition, is preferably 1 $\mu$M to $10^2$ $\mu$M. The amount of naphthaleneacetic acid is more preferably 1 to 10 $\mu$M. That range is preferred, because if the amount is less 1 $\mu$M or $10^2$ $\mu$M, it is difficult to maintain the high re-differentiation.

In addition, the culture medium may contain a very small amount of organic material(s), carbon source, etc. ordinarily used in culturing. As a very small amount of the organic material(s), mention may be made of vitamins such as vitamin B1, B6, nicotinic acid, thiamine hydrochloric acid salt, and pyridoxine hydrochloric acid salt; amino acid such as glycine and asparagine; and hexavalent alcohols such as inositol and sorbitol.

Saccharides such as sucrose and glucose may be recited as the carbon source. Tissue pieces planted in the culture medium can be cultured in a dark place or a bright place in a temperature range of 22 to 28° C. The temperature range is more preferably 24 to 26° C. Callus begins to be formed about one week after starting the culturing. It may be observed that multiple shoots are redifferentiated about 2 weeks after the callus is observed. The callus and the polyblast obtained can be subcultured every two weeks, for example.

The tissue-culturing method according to the present invention can be effected by subculturing the cultured cells of the Australian laurel, Pittosporaceae having the undifferential power in the culture containing thidiazuron (TDZ). With respect to the amount of thidiazuron, the condition employed for culturing thee cultured cells as mentioned above may be employed.

As the cultured cells of the Australian laurel, Pittosporaceae having the undifferential power, the above cultured cells in the present invention may be used.

In the tissue-culturing method of the present invention, naphthaleneacetic acid (NAA) may be incorporated into the culture medium. With respect to the amount of naphthaleneacetic acid, the limitation recommended in the above-mentioned culturing of the cultured cells may be also adopted.

Next, the cultured cell into which a foreign material is introduced according to the present invention will be explained. In order to introduce such a foreign material into the cultured cell in the present invention, an ordinary foreign material-introducing method may be used. For example, a foreign material-introducing method employing laser is known (JP-A 62-7387). Such a laser-employing method may be used to introduce the foreign material into the cultured cell according to the present invention. In order to introduce a gene into the cultured cell, there are broadly known a method for inserting it directly into a cultured cell with use of a fine glass tube (microinjection method), a method based on a cell fusion (liposomee method and protoplast fusion method), an introducing method using a infection process (Agrobacterium method), a method for promoting membrane permeability (electropolation method), etc. There is also known a gene gum method in which a fine metal particle coated with DNA is delivered into a living cell at a high speed to introduce the gene into the cell through a cell wall and a cell membrane. The gene can be introduced into the cultured cell according to the present invention by using any one of the above gene-introducing method.

In the case of the Australian laurel, Pittosporaceae tissue in which a foreign material is introduced into a living cell of an explant of the seedling of the Australian laurel, Pittosporaceae, good strains and new varieties can be propagated by culturing the tissue. The term "seedling" means a juvenile plant germinated from a seed of a seed plant. In most cases, it refers to those retaining cotyledons or a first leaves.

The actually living cut piece is not particularly limited, but any actually living cut pieces before and after the formation of a callus from a tissue piece and before and after the formation of multiple shoots may be used. The actually living cut piece before the formation of the callus is preferred from the standpoint of effectively expressing the foreign material.

As the foreign material, at least one material selected from the group consisting of a hereditable material, a protein, an organelle, a physiologically active material, a RNA, an oligonucleotide, a nucleic acid analog and an indicator may be recited.

As the hereditable material, at least one material selected from the group consisting of a DNA, a plasmid, a chromosome, a artificial chromosome, and an organelle DNA may be recited.

EXAMPLES

The present invention will be explained in more detail based on specific examples, but it is not intended that the invention should be interpreted as being limited to the following examples.

Example 1

A WP culture medium or a MS culture medium was used as a fundamental culture medium. As a carbon source was used 1% sucrose, and 0.3% Gellan-Gum (Trade name) was used as a gelling agent. An Australian laurel, Pittosporaceae seed was treated with 70% ethanol for 1 hour with 2.5% sodium hypochlorite for 1 hour, and sterilized by washing it with sterilized water. After water was fed to the seed 2 night or more at 4° C. in dark, it was planted in the culture medium. After germination, a seedling of four weeks age was used for a tissue culturing. Cut pieces, 1 mm thick, were prepared from a leave, a stem and a roof of the living matter, and planted and cultured in the same culture medium as mentioned above but containing naphthaleneacetic acid and thidiazuron (TDZ) as a hormon. Ten days after starting the culturing, it was confirmed that multiple shoots were formed from the cut pieces. About 2 months after the planting, a shoot was cut out from the polyblast, and indoleacetic acid was applied to a cut portion of the shoot. The shoot treated with indoleacetic acid was inserted into a solid culture medium or a mixed soil of perlite and vermiculite containing a culture medium. The shoot was cultured and rooted. After culturing for a given time period, a plant in which roots were observed to grow from the cut portion was used as a seedling.

Cut pieces from the stem was cultured in the WP culture medium added with thidiazuron and naphthaleneacetic acid for 6 weeks, and observation results thereof are shown in Table 1.

TABLE 1

| TDZ concentration ($\mu$m) | NAA concentration ($\mu$M) | Numbers of cut pieces leading to stem or leaf/10 cut pieces |
|---|---|---|
| 0.1 | 0 | 0 |
| 0.1 | 1 | 0 |
| 0.1 | 2 | 0 |
| 0.1 | 3 | 0 |
| 0.1 | 4 | 0 |
| 0.1 | 5 | 0 |
| 10 | 0 | 0 |
| 10 | 1 | 5 |
| 10 | 2 | 8 |
| 10 | 3 | 7 |
| 10 | 4 | 5 |
| 10 | 5 | 6 |

As is clear from Table 1, when the concentration of thidiazuron is not less than 10 $\mu$M, redifferentiation was confirmed with respect to the culture medium containing naphthaleneacetic acid.

Example 2

Next, a gene was introduced into a cultured cell. That is, after cut pieces obtained from the leaf, the stem and the root were cultured in the culture medium containing the hormone for a given time period, the gene was introduced in each of the cut pieces. By further culturing them, Australian laurel, Pittosporaceae plants bearing an introduced foreign gene were prepared in trial.

In order to prepare the gene-introduced Australian laurel, Pittosporaceae plant, the gene was introduced into a cut piece of a living stem of the Australian laurel, Pittosporaceae according to the particle gun method. The cut piece of the living stem was one in which no callus was formed. The gene in which a gene having Hygromicin resistance was incorporated as a selection marker and an indicator in addition to the intended gene was introduced into the cut piece of the living stem. The Australian laurel, Pittosporaceae shoot was selected by relying upon the above marker gene. The Australian laurel, Pittosporaceae into which the gene was introduced was subjected to the tissue culturing in the same manner as in Example 1. A microscope photograph of an appearance of the Australian laurel, Pittosporaceae into which the gene was introduced is shown in FIG. 1. The presence of the gene in the cell was confirmed by using the PCR method.

Example 3

Redifferentiation from the leaf and the stem of the Australian laurel, Pittosporaceae was examined. The WP culture medium was used as a culture medium. A culturing temperature was set in a range of 22 to 28° C. The Australian laurel, Pittosporaceae was cultured in a bright place. The planting condition and the other culturing conditions were the same as those in Example 1. Results are shown in Table 2.

TABLE 2

| | | Redifferentiation | |
|---|---|---|---|
| TDZ (nM) | NAA ($\mu$M) | Leaf (%) | Embryo (%) |
| $10^4$ | 0 | 0 | 5.0 |
| $10^4$ | 1.07 | 0 | 40.0 |
| $10^4$ | 2.15 | 0 | 85.0 |
| $10^4$ | 3.22 | 0 | 75.0 |
| $10^4$ | 4.30 | 0 | 55.0 |
| $10^4$ | 5.37 | 0 | 70.0 |
| $10^5$ | 0 | 0 | 10.0 |
| $10^5$ | 1.07 | 0 | 35.0 |
| $10^5$ | 2.15 | 5.0 | 35.0 |
| $10^5$ | 3.22 | 5.0 | 60.0 |
| $10^5$ | 4.30 | 5.0 | 35.0 |
| $10^5$ | 5.37 | 0 | 65.0 |

As is clear from the results in Table 2, considerably high redifferentiation percentages were realized in the case of culturing with the cultures containing $10^4$ to $10^5$ nM thidiazuron.

Example 4

Under the same conditions as in Example 1, Australian laurel, Pittosporaceae was germinated and grown in a sterilized state on the culture medium, and cut pieces were prepared from leaves, stems and roots of seedlings at 8 weeks and 23 weeks after starting the culturing. The redifferentiation percentages several weeks after planting were checked by using these cut pieces.

A tissue piece was planted in the culture medium, and the formed percentage of the multiple shoots and the state of the callus observed 6 weeks thereafter. The redifferentiation condition was examined by using benzyladenin (BA), thidiazuron (TDZ), naphthaleneacetic acid (NAA), indoleacetic acid (IAA), and 2,4-dichloropenoxyacetic acid (2,4-D) were used. Further, examinations were effected for single use or combined use of the above hormones at various concentrations. As a fundamental culture medium, the MS culture medium or the WP culture medium was used. Subculturing was effected every two weeks, and the subculturing was effected in the same culture medium.

When a part of the cheeseweed tissue was cultured in the culture containing TDZ and NAA as the hormone, the callus induction and the redifferentiation induction occurred on the same culture medium. The callus was propagated until about 3 weeks after the cut piece was planted on the culture medium. Thereafter, the multiple shoots were formed, which confirmed the redifferentiation induction. On the other hand, a callus softer than the callus having formed the multiple shoots was formed when the culturing was effected on a culture medium containing TDZ and 2,4-D. However, in this case, no multiple shoots were formed even when the culturing was continued on the same culture under the same condition.

It was also confirmed that the redifferentiation power of the calluses induced from the stem was higher as compared with the leaf and the root with respect to the Australian laurel, Pittosporaceae tissues.

When seedlings at 8 weeks and 23 weeks after planting following the sterilized germination and growing on the WP culture medium were used as starting materials, that at 8 weeks after the planting effectively form the multiple shoots.

In summary, comparison in the redifferentiation power revealed that a case in which a cross-cut piece of the stem obtained from the living matter art 8 weeks after the planting was cultured on the WP culture containing TDZ and NAA exhibited a highest differentiation result.

The cultured cells according to the present invention has the advantageous effects that the tissue culturing of the Australian laurel, Pittosporaceae can be effectively performed, and the plants having high redifferentiation power can be regenerated.

Further, the culture cell according to the present invention has the advantageous effect that the cell can be used for the propagation of superior strains and the introduction of a foreign gene.

What is claimed is:

1. A method for regenerating a *Pittosporum tobira* plantlet, said method comprising the step of subculturing a mass of cultured plant cells or tissue in a culture medium containing thidiazuron (TDZ) in an amount effective for inducing callus formation.

2. A method according to claim 1, wherein the tissue has an age of less then 8 weeks after seeding.

3. A method according to claim 2, wherein the tissue is obtained by aseptically growing seed.

4. A method according to claim 3, wherein the tissue comprises a foreign material.

5. A method according to claim 4, wherein the foreign material is at least one material selected from the group consisting of a heritable material, a protein, an organelle, a physiologically active material, and an indicator.

6. A method according to claim 5, wherein the heritable material is at least one material selected from the group consisting of a DNA, a plasmid, a chromosome, an artificialchromosome, and an organelle DNA.

7. A method according to claim 5, wherein the foreign material is at least one material selected from the group consisting of an RNA, an oligonucleotide and a nucleic acid analog.

8. A method according to claim 1, wherein the culture medium further comprises naphthaleneacetic acid (NAA).

9. A method according to claim 2, wherein the culture medium further comorises naphthaleneacetic acid (NAA).

10. A method according to claim 3, wherein the culture medium further comprises naphthaleneacetic acid (NAA).

11. A method according to claim 4, wherein the culture medium further comprises naphthaleneacetic acid (NAA).

12. A method according to claim 5, wherein the culture medium further comprises naphthaleneacetic acid (NAA).

13. A method according to claim 6, wherein the culture medium further comprises naphthaleneacetic acid (NAA).

* * * * *